United States Patent [19]

Mitra et al.

[11] Patent Number: 5,154,762
[45] Date of Patent: Oct. 13, 1992

[54] UNIVERSAL WATER-BASED MEDICAL AND DENTAL CEMENT

[75] Inventors: Sumita B. Mitra; Smarajit Mitra, both of West St. Paul, Minn.

[73] Assignee: Minnesota Mining and Manufacturing Company, St. Paul, Minn.

[21] Appl. No.: 708,988

[22] Filed: May 31, 1991

[51] Int. Cl.⁵ .................................. C09K 3/00
[52] U.S. Cl. ........................ 106/35; 523/116
[58] Field of Search ............ 106/35; 523/116

[56] References Cited

U.S. PATENT DOCUMENTS

| | | | |
|---|---|---|---|
| 3,655,605 | 4/1972 | Smith et al. | 260/29.6 |
| 3,814,717 | 6/1974 | Wilson et al. | 260/29.6 |
| 4,043,327 | 8/1977 | Potter et al. | 128/89 |
| 4,143,018 | 3/1979 | Crisp et al. | 260/29.6 |
| 4,209,434 | 6/1980 | Wilson et al. | 260/29.6 |
| 4,243,567 | 1/1981 | Potter | 260/29.6 |
| 4,539,382 | 9/1985 | Omura et al. | 526/276 |
| 4,867,817 | 9/1989 | Kneafsey et al. | 156/73.1 |
| 4,872,936 | 10/1989 | Engelbrecht | 156/307.3 |

FOREIGN PATENT DOCUMENTS

| | | |
|---|---|---|
| 46717/89 | 6/1990 | Australia. |
| 0323120 | 7/1989 | European Pat. Off. |
| 0329268 | 8/1989 | European Pat. Off. |
| 0391619 | 10/1990 | European Pat. Off. |

OTHER PUBLICATIONS

"Redox Polymerization", G. S. Misra and U. D. N. Bajpai, Prog. Polym. Sci., 8, 61–131 (1982).
Wilson, A. D. et al Glass–Ionomer Cement, Quintessence Publishing Co., Inc. (1988), p. 51.

Primary Examiner—Shrive Beck
Assistant Examiner—Margaret Einsmann
Attorney, Agent, or Firm—Gary L. Griswold; Walter N. Kirn; David R. Cleveland

[57] ABSTRACT

Dental cement containing water, acid-reactive filler, water-miscible acidic polymer, an ethylenically-unsaturated moiety, photoinitiator, water-soluble reducing agent and water-soluble oxidizing agent. The cement has three curing modes, namely an acid-filler ionic reaction, a photoinitiated crosslinking reaction and a redox-initiated crosslinking reaction. The cement cures well in thick layers, and can be used without a dental curing light or with a light that is weak or defective.

22 Claims, No Drawings

UNIVERSAL WATER-BASED MEDICAL AND DENTAL CEMENT

TECHNICAL FIELD

This invention relates to water-based medical and dental cements.

BACKGROUND ART

Resin-based composite and restorative materials generally have very high cohesive strength, and accordingly are widely used in dentistry. However, in recent years there has been a resurgence in water-based cements. These water-based cements may contain resinous components, but are distinguished by containing substantial amounts of water. Examples include metal oxide cements such as those described in U.S. Pat. No. 3,655,605 and fluoroaluminosilicate glass cements (also known as "glass ionomer cements") such as those described in Example 6 of the '605 patent and in U.S. Pat. Nos. 3,814,717, 4,043,327, 4,143,018, and 4,209,434. These water-based cements have also found utility in medical applications such as the fabrication of orthopedic bandages, as described in U. S. Pat. Nos. 4,043,327 and 4,243,567.

Typically, these cements are cured or hardened by combining a polyfunctional acid, water and an acid-reactive metal oxide or glass filler. Hardening occurs due to the reaction between the acidic groups of the polyfunctional acid and cations leached from the filler. More recently, light-curable water-based cements have appeared. Examples are shown in U.S. Pat. No. 4,872,936, European Pat. Application Nos. 0 323 120 and 0 329 268 and Australian Published Pat. Specification No. 46717/89. These light-curable cements include one or more ethylenically-unsaturated components and a suitable photoinitiator. Hardening takes place independently from the acid-filler reaction mentioned above via crosslinking of the ethylenically-unsaturated component upon exposure of the photoinitiator to light or other activating energy.

A light-curable and apparently anhydrous cement is shown in European Pat. Application No. 0 391 619. It contains a number of ingredients, including benzoyl peroxide.

Although light-curable cements have many advantages, they do require use of a light. If the light is defective (for example, due to breakage or discoloration of the filters typically installed in the light path or through deterioration of the curing lamp), then the composition may undergo incomplete light-curing polymerization. Also, owing to the need to insure adequate penetration of the light energy into the cement, thick restorations typically must be built up in separately cured thin layers. In some dental applications it may be impractical to use a curing light. For example, when luting a metallic crown to a prepared tooth stump, light typically will not penetrate underneath the crown. Likewise, for endodontic applications, light may not penetrate the full depth of the endodontic preparation. On the other hand a cement that cures only by dark reactions takes a long time to cure. During this time the cement may be prone to moisture contamination.

Accordingly, presently available cements have not had universal applicability. This has led to the appearance of many special-purpose products in the marketplace, with attendant need for the practitioner to maintain separate inventories of each cement, to undergo training in the use of more than one cement, and to avoid improper use through inadvertent selection of the wrong cement.

SUMMARY OF THE INVENTION

The present invention provides a cement having three curing modes. The cement cures through a first mechanism, via an acid-filler ionic reaction. The cement cures through a second mechanism, via photoinitiated free radical crosslinking of an ethylenically-unsaturated component. Finally, the cement cures through a third mechanism, via redox-initiated free radical crosslinking of the ethylenically-unsaturated component. The cement can be used in a wide variety of applications, and will provide good results even if a dental curing light is not used or is improperly used. The cement is water-based, and thus can be used under moist conditions such as are typically present in the mouth.

The invention provides, in one aspect, a water-containing, ionically-hardenable, photocurable, ethylenically-unsaturated dental cement, comprising
a) finely-divided acid-reactive filler,
b) water-miscible acidic polymer,
c) photoinitiator,
d) water-soluble reducing agent, and
e) water-soluble oxidizing agent.
Preferably, the reducing agent and the oxidizing agent are capable of initiating gelation of a 10:10:1 (weight basis) water:acrylamide:methylene bis-acrylamide mixture.

In a further aspect, the invention provides preferred cements in which the reducing agent or the oxidizing agent are contained in microcapsules. The microcapsules improve shelf life and facilitate packaging.

DETAILED DESCRIPTION

Generally, the cements of the invention are formulated in two parts, although formulations employing three or more parts can be made up if desired. In a two part formulation, the first part typically is a powder portion containing the acid-reactive filler. The second part typically is a liquid portion containing the acidic polymer, water and one (but usually not both) of the water-soluble reducing agent and water-soluble oxidizing agent. If the reducing agent is present in the liquid portion, then the oxidizing agent is typically present in the powder portion, and vice-versa. The reducing agent and oxidizing agent can be combined in the powder portion or in the liquid portion through the use of a microencapsulation technique described in more detail below.

The invention is not limited to powder:liquid formulations. For example, one part anhydrous formulations containing filler, polymer, photoinitiator, reducing agent and oxidizing agent can be prepared. These can be sold in dry form and prepared for use by adding water. Also, two part paste:paste formulations can be prepared by adding to the acid-reactive filler a suitable polymerizable liquid that does not react with that filler (e.g., 2-hydroxyethyl methacrylate, or "HEMA"), yielding a first paste. The acidic polymer described above is combined with a suitable filler that does not react with the acidic polymer (e.g., ground quartz), yielding a second paste. The two pastes are prepared for use by stirring them together. Other useful configurations will be familiar to those skilled in the art. However, for simplicity, the remainder of this patent specification will refer to powder:liquid formulations unless specifically noted otherwise.

The cements of the invention contain water. The water can be present in the product as sold, or added by the dentist just prior to use. The water can be distilled, deionized or plain tap water. Generally, deionized water is preferred. The amount of water should be sufficient to provide adequate handling and mixing properties and to permit the transport of ions in the filler-acid reaction. Preferably, water represents at least about 1%, more preferably about 3% to about 25%, and most preferably about 5% to about 20% of the total weight of ingredients used to form the cement.

The cements of the invention are ionically hardenable. By this is meant that they contain ingredients that, when combined, can react via an ionic reaction to produce a hardened mass. The ionic reaction occurs between acid groups on the polymer and acid-reactive groups on the filler.

The cements of the invention are also ethylenically-unsaturated. In other words, they contain at least one ethylenically-unsaturated moiety. The ethylenically-unsaturated moiety can be present as a separate ingredient (for example, as an acrylate- or methacrylate-functional monomer) or it can, if desired, be present as a group on another ingredient such as the acidic polymer. A wide variety of ethylenically-unsaturated moieties can be used. A useful list of suitable materials is shown at page 9, line 13 through page 13, last line of Australian Published Pat. Specification No. 46717/89. Of the many materials mentioned, water-miscible or water-soluble acrylates and methacrylates such as 2-hydroxyethyl methacrylate, hydroxymethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, polyethylene glycol dimethacrylate, urethane methacrylates, acrylamide, methacrylamide, methylene bisacrylamide or methacrylamide, and diacetone acrylamide and methacrylamide are preferred. Mixtures of ethylenically-unsaturated moieties can be used if desired. Preferably, the ethylenically-unsaturated moieties are present as groups on the acidic polymer, as described in more detail below.

The cements of the invention also contain an acid-reactive filler. The filler should be sufficiently finely-divided so that is can be conveniently mixed with the other ingredients and used in the mouth. Preferred average particle diameters for the filler are about 0.2 to about 15 micrometers, more preferably about 1 to 10 micrometers, as measured using, for example, a sedimentation analyzer.

Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred. Suitable fillers are also available from a variety of commercial sources familiar to those skilled in the art. For example, suitable fillers can be obtained from a number of commercially available glass ionomer cements, such as "GC Fuji LC" cement and "Kerr XR" ionomer cement. Mixtures of fillers can be used if desired.

If desired, the filler can be subjected to a surface treatment. Suitable surface treatments include acid washing, treatment with phosphates, treatment with chelating agents such as tartaric acid, treatment with a silane as described in Australian Published Pat. No. 46717/89, and treatment with an acidic silanol solution.

The amount of filler should be sufficient to provide a cement having desirable mixing and handling properties before cure, and good performance after cure. Preferably, the filler represents less than about 90%, more preferably about 25% to about 85%, and most preferably about 50% to about 75% by weight of the total weight (including water) of the unset cement components.

The acidic polymer need not be entirely water soluble, but it should be at least sufficiently water-miscible so that it does not undergo substantial sedimentation when combined with the liquid ingredients of the cement. Suitable acidic polymers include those listed at column 2, line 62 through column 3, line 6 of U.S. Pat. No. 4,209,434. Preferred acidic polymers include homopolymers and copolymers of alkenoic acids such as acrylic acid, itaconic acid and maleic acid. Suitable polymers are also available from a wide variety of commercial sources, and many are found in currently-available glass ionomer cements. As will be appreciated by those skilled in the art, the polymer should have a molecular weight sufficient to provide good storage, handling and mixing properties. A preferred molecular weight is about 5000 to about 100,000 weight average molecular weight ($\overline{M}_w$), evaluated against a polystyrene standard using gel permeation chromatography. Preferably, the acidic polymer contains one or more ethylenically-unsaturated groups. Suitable ethylenically-unsaturated acidic polymers are described in U.S. Pat. No. 4,872,936 and in European Pat. Application No. 0 323 20. Preferably, the numbers of acid groups and ethylenically-unsaturated groups are adjusted to provide an appropriate balance of properties in the cement, both during the setting reaction and after the cement has hardened. Acidic polymers in which about 10 to about 30% of the acidic groups have been replaced with ethylenically-unsaturated groups are preferred.

The amount of acidic polymer in the cement should also be sufficient to provide a desired balance of physical properties. A preferred acidic polymer amount is at least about 5%, more preferably about 10 to about 50%, and most preferably about 10 to about 30% of the total weight (including water) of the unset cement components.

The photoinitator should be capable of promoting free radical crosslinking of the ethylenically-unsaturated component on exposure to light of a suitable wavelength and intensity. It also preferably is sufficiently shelf-stable and free of undesirable coloration to permit its storage and use under typical dental conditions. Visible light photoinitiators are preferred. The photoinitiator preferably is water-soluble or water-miscible. Photoinitiators bearing polar groups usually have a sufficient degree of water-solubility or water-miscibility. The photoinitiator frequently can be used alone but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from CibaGeigy Corp.

The photoinitiator should be present in an amount sufficient to provide the desired rate of photopolymerization. This amount will be dependent in part on the light source, the thickness of the cement layer to be exposed to radiant energy and the extinction coefficient of the photoinitiator. Typically, the photoinitiator components will be present at a total weight of about 0.01 to about 5%, more preferably from about 0.1 to about 5%, based on the total weight (including water) of the unset cement components. The photoinitiator can be included in either the paste or liquid parts of the cement.

The water-soluble reducing agent and water-soluble oxidizing agent are most conveniently discussed together. They should react with or otherwise cooperate with one another to produce free-radicals capable of initiating polymerization of the ethylenically-unsaturated moiety. The reducing agent and oxidizing agent preferably are sufficiently shelf-stable and free of undesirable colorization to permit their storage and use under typical dental conditions. They should be sufficiently water-soluble to permit ready dissolution in (and discourage separation from) the other components of the cement. The reducing agent and oxidizing agent should also be sufficiently soluble and present in an amount sufficient to permit an adequate free-radical reaction rate. This can be evaluated by combining all of the ingredients of the cement except for the filler under safelight conditions, and observing whether or not a hardened mass is obtained.

The reducing agent and oxidizing agent preferably are sufficiently water-soluble and have sufficient reduction and oxidation potentials to initiate gelation of an aqueous crosslinkable acrylamide solution. This can be evaluated by adding 2 weight % each of the reducing agent and the oxidizing agent to an aqueous acrylam bis-acrylamide solution (described below in Table Ia and observing whether or not gelation occurs within 30 minutes. Useful reducing agent/oxidizing agent pairs are shown in "Redox Polymerization", G. S. Misra and U. D. N. Bajpai, *Prog. Polym. Sci.*, 8, 61–131 (1982).

Preferred reducing agents include ascorbic acid, cobalt (II) chloride, ferrous chloride, ferrous sulfate, hydrazine, hydroxylamine (depending upon the choice of oxidizing agent) oxalic acid, thiourea, and salts of a dithionite or sulfite anion. Preferred oxidizing agents include cobalt (III) chloride, tert-butyl hydroperoxide, ferric chloride, hydroxylamine (depending upon the choice of reducing agent), perboric acid and its salts, and salts of a permanganate or persulfate anion. Hydrogen peroxide can also be used, although it has been found to interfere with the photoinitiator in some instances.

The amount of reducing agent and oxidizing agent should be sufficient to provide the desired degree of polymerization of the ethylenically-unsaturated component. The preferred amount for each of the reducing agent and oxidizing agent is about 0.01 to about 10%, more preferably about 0.02 to about 5%, based on the total weight (including water) of the unset cement components.

As mentioned above, the reducing agent or the oxidizing agent can be microencapsulated. This will generally enhance shelf stability and permit packaging both the reducing agent and oxidizing agent together. For example, through appropriate selection of the encapsulant, both the oxidizing agent and reducing agent can be combined with the filler and kept in a storage-stable state. Likewise, through appropriate selection of a water-insoluble encapsulant, the reducing agent and oxidizing agent can be combined with water and the acidic polymer and maintained in a storage-stable state.

Either water-soluble or water-insoluble encapsulants can be employed. However, water-insoluble encapsulants are preferred, as they generally provide better long term storage stability under moist or humid conditions Although the use of a water-insoluble encapsulant may initially seem inappropriate in a water-based cement, it has been found that vigorous mechanical mixing generally will be sufficient to break apart the capsule walls and permit adequate release of the encapsulated reducing agent or oxidizing agent and subsequent cure of the cement.

Preferably the encapsulant is a medically acceptable polymer and a good film former. Also, the glass transition temperature ($T_9$) of the encapsulant preferably is above room temperature.

A wide variety of encapsulants can be used, with cellulosic materials as cellulose acetate, cellulose acetate butyrate, ethyl cellulose, hydroxymethyl cellulose and hydroxyethyl cellulose being preferred. Other encapsulants include polystyrene, copolymers of polystyrene with other vinylic monomers, polymethylmethacrylate, copolymers of methylmethacrylate with other ethylenically-unsaturated monomers, and other materials that will be familiar to those skilled in the art of encapsulation.

The capsules themselves need not be perfectly spherical nor uniformly shaped. It is merely sufficient that they entrain or entrap the encapsulated reducing agent or oxidizing agent in a manner sufficient to permit storage of the encapsulated material in a cement component without leading to undesirable premature polymerization.

To encapsulate the reducing agent or oxidizing agent in a water-insoluble encapsulant, it is preferred to dissolve the encapsulant in a suitable water-immiscible solvent such as methyl acetate, ethyl acetate or methylene chloride. Meanwhile, the reducing agent or oxidizing agent is dissolved in water. The water solution can then be added to the solution of encapsulant and water-immiscible solvent. Stirring or other high speed shear techniques preferably are used to promote uniform microcapsule formation. The capsule shells are formed around the aqueous solution droplets either by evaporation of the water-immiscible solvent or by the addition of a second water-immiscible solvent (e.g., n-hexane)

that will precipiate the encapsulant. The capsules can then be removed by cooling and filtration.

To encapsulate the reducing agent or oxidizing agent in a water-soluble encapsulant, the dry reducing agent or oxidizing agent is preferably suspended in a stirred solution of the encapsulant in a water-immiscible organic solvent. Vigorous stirring will promote uniform encapsulation of the reducing agent or oxidizing agent. The capsules can be formed by evaporation or by precipitation and then removed using the techniques described above.

If desired, the cements of the invention can contain adjuvants such as pigments, nonvitreous fillers, inhibitors, accelerators, viscosity modifiers, surfactants, and other ingredients that will be apparent to those skilled in the art.

The cements of the invention can be mixed and clinically applied using conventional techniques. However, the cements will have particular utility in clinical applications where cure of a conventional light-curable cement may be difficult to achieve. Such applications include deep restorations, large crown build-ups, endodontic restorations, luting of metallic crowns or other light-impermeable prosthetic devices to teeth, and other restorative applications in inaccessible areas of the mouth. The three-way cure mechanism facilitates thorough, uniform cure and retention of good clinical properties. The cements of the invention thus show good promise as a universal restorative.

The cements of the invention are further described in the following illustrative examples, which should not be construed as limiting the scope of the invention. Unless otherwise indicated, all parts and percentages are on a weight basis.

EXAMPLE 1

Cements Prepared Using Various Curing Modes

A test solution was prepared by combining the ingredients set out below in Table Ia:

TABLE Ia

| Ingredients | Parts |
|---|---|
| Acrylamide | 30 |
| Methylene bis-acrylamide | 3 |
| Water | 30 |

In a series of four runs a 2 g portion of the test solution was placed in a glass test tube. For each run, 2% of the ingredients set out below in Table Ib were added to a separate test tube with shaking:

TABLE Ib

| Run No. | Added Ingredients |
|---|---|
| 1 | Potassium Persulfate |
|   | Ascorbic Acid |
| 2 | Potassium Persulfate |
|   | Thiourea |
| 3 | Potassium Persulfate |
|   | Oxalic Acid |
| 4 | Ammonium Persulfate |
|   | Ascorbic Acid |

The contents of the two test tubes were combined with shaking. For each run, gelation and an exotherm were observed within seven minutes.

The ingredients set out below in Table IIa were mixed, melted in an arc furnace at about 1350°–1450° C., poured from the furnace in a thin stream and quenched using chilled rollers to provide an amorphous single-phase fluoroaluminosilicate glass:

TABLE IIa

| Ingredient | Parts |
|---|---|
| $SiO_2$ | 37 |
| $AlF_3$ | 23 |
| $SrO$ | 20 |
| $Al_2O_3$ | 10 |
| $AlPO_4$ | 7 |
| $Na_2AlF_6$ | 6 |
| $P_2O_5$ | 4 |

The glass was ball-milled to provide a pulverized frit with a surface area of 2.6 $m^2/g$ measured using the Brunauer, Emmet and Teller (BET) method. The pulverized glass was labeled "Control Glass". 20 Parts of the Control Glass were mixed with a solution of 0.1 parts ascorbic acid (a water-soluble reducing agent) in 39.5 parts methanol, and stirred for 10 minutes using a magnetic stirrer. The wet glass was poured into a dish to a depth less than 1 cm, and then dried in a 45° C. oven for 16 hours. The dried glass was sieved through a 74 $\mu$m mesh screen, and labeled "Glass A".

The ingredients set out below in Table IIb were mixed using a paint shaker to provide two cement-forming liquids labeled "Control Liquid" and "Liquid A". Each liquid contained ethylenically-unsaturated components (as groups on the copolymer and as a separate ingredient), and carboxylic acid (as groups on the copolymer). Liquid A also contained potassium persulfate (a water-soluble oxidizing agent):

TABLE IIb

| | Cement-forming liquids, parts | |
|---|---|---|
| Ingredient | Control Liquid | Liquid A |
| Copolymer[1] | 50 | 50 |
| Water[2] | 30 | 30 |
| HEMA[3] | 20 | 20 |
| $(C_6H_5)_2I^+PF_6^-$ | 0.7 | 0.7 |
| CPQ[4] | 0.25 | 0.25 |
| BHT[5] | 0.1 | 0.1 |
| $K_2S_2O_8$ | — | 0.05 |

[1]Ethylenically-unsaturated acidic copolymer prepared like the precipitated dry polymer of EXAMPLE 11 of European Published Pat. Application No. 0 323 120.
[2]Distilled water.
[3]2-Hydroxyethyl methacrylate.
[4]Camphorquinone.
[5]Butylated hydroxytoluene.

The absorbic acid-treated Glass A and the potassium persulfate-containing Liquid A were hand-spatulated at a 1.4:1 powder:liquid ratio. The resulting cement exhibited good mixing properties and a two minute working time. The end of the working period coincided with a loss of gloss and a marked decrease in tack.

In a series of 4 runs, the glasses Control Glass and Glass A, and the liquids Control Liquid and Liquid A, were hand-spatulated for one minute at a 1.4:1 powder:liquid ratio, then packed into a 4 mm inside diameter glass tube, capped with silicone rubber plugs, and axially compressed at about 0.28 MPa. About 1.5 minutes after the start of mixing, samples for the cements of Runs nos. 1 and 3 were exposed for 80 seconds to light from two oppositely-disposed visible light curing lamps ("VISILUX 2" curing lamp, 3M) and then the axial pressure was removed. The cements of Run nos. 2 and 4 were allowed to remain under pressure for 10 minutes and were not photopolymerized.

Each of the cements of Run nos. 1–4 was allowed to stand for one hour at ambient pressure, 90%+ relative humidity and 37° C. The samples were cut on a diamond saw to form cylindrical plugs 2 mm long for measurement of Diametral tensile strength ("DTS"), and 8 mm long for measurement of compressive strength ("CS"). The plugs were stored in distilled water at approximately 37° C. for about 24 hours. DTS and CS values were determined for 5 samples of each cement according to ISO specification 7489.

The results are set out below in Table III, along with a brief identification of the applicable cure mechanism for each sample.

TABLE III

| Run No. | Glass | Liquid | Photo Curing | Cure Mechanism | CS | DTS |
|---|---|---|---|---|---|---|
| 1 | Glass A | Liquid A | Yes | IPR[1] | 154 | 27 |
| 2 | Glass A | Liquid A | No | IR[2] | 141 | 20 |
| 3 | Control Glass | Control Liquid | Yes | IP[3] | 155 | 26 |
| 4 | Control Glass | Control Liquid | No | I[4] | 37 | 3 |

[1]IPR = Acid-base ionomer reaction ("I") plus photoinitiated reaction ("P") plus redox reaction ("R").
[2]IR = I reaction plus R reaction.
[3]IP = I reaction plus P reaction.
[4]I = I reaction.

The results in Table III illustrate the improvement provided by the invention. When a cement of the invention was cured using all three cure mechanisms (Run no. 1), CS and DTS were experimentally equivalent to the values obtained for a light-curable ionomer cement cured in thin section using two cure mechanisms (Run no. 3). When the photoinitiated "P" mechanism was omitted but the redox "R" reaction was present (Run no. 2), CS and DTS were maintained at respectably high levels. This would correspond to curing a cement of the invention in a very thick section, or to curing it without a properly-operating curing lamp. With or without photocuring, the cement of the invention had substantially better CS and DTS than a cement cured using only the ionomer "I" reaction (Run no. 4). Thus a cement of the invention could be cured without a curing lamp, or with a defective curing lamp, and still provide a strong cured cement.

In a further comparison, the Control Liquid was combined with 0.05% benzoyl peroxide and shaken on a paint mixer for two days. The peroxide did not dissolve, demonstrating that a water-soluble oxidizing agent was required even though the Control Liquid contained a substantial portion of nonaqueous resin.

EXAMPLE 2

Comparison of Dentin Adhesion Using Various Curing Modes

Five bovine teeth of similar age and appearance were partially embedded in circular acrylic disks so that the enamel was exposed. The exposed portion of each tooth was ground flat and parallel to the acrylic disc using Grade 120 silicon carbide paper-backed abrasive mounted on a lapidary wheel, until the dentin was exposed Further grinding and polishing of the teeth was carried out by mounting Grade 320 silicon carbide paper-backed abrasive on the lapidary wheel. During the grinding and polishing steps, the teeth were continuously rinsed with water. The polished teeth were stored in distilled water and used for testing within 2 hours after polishing. The polished teeth were removed from the water and dried using a stream of compressed air.

A mold made from a 2.5 mm thick "TEFLON" polytetrafluoroethylene sheet with a 5 mm diameter circular hole through the sheet was clamped to each polished tooth so that the central axis of the hole in the mold was normal to the polished tooth surface. The mold was fitted with a sleeve made from a no. 4 gelatin capsule. The sleeve was filled with a hand-spatulated glass ionomer cement mixture. The cement was light-cured for 60 seconds, allowed to stand for about 5 minutes at room temperature, then stored in distilled water at 37° C. for 24 hours. Dark-cured samples were not photocured, but were allowed to stand at room temperature under a yellow safelight for 15 minutes before placing them in water. The molds were then carefully removed, leaving a molded cement button attached to each tooth.

Adhesive strength was evaluated by mounting the acrylic disk in a holder clamped in the jaws of an "INSTRON" tensile testing apparatus with the polished tooth surface oriented parallel to the direction of pull. A loop of 0.44 mm diameter orthodontic wire was placed around the base of the cement button adjacent to the polished tooth surface. The ends of the orthodontic wire were clamped in the pulling jaw of the tensile testing apparatus, placing the bond in shear stress. The bond was stressed until it (or the cement button) failed, using a crosshead speed of 2 mm/min and an average of 5 or more samples.

A freshly-mixed sample made from a 1.4:1 mixture of Glass A and Liquid A was evaluated for adhesion to dentin using the procedure described above. With photocuring, the average measured adhesive shear bond strength for 6 samples was 8.9 MPa. If photocuring was omitted, the average measured shear bond strength dropped to 2.9 MPa. A control cement prepared from the Control Glass and the Control Liquid had an average measured adhesive shear bond strength of 4.6 MPa. If photocuring was omitted, the average measured adhesive shear bond strength dropped to less than 1 MPa. Accordingly, use of a cement with all three cure modes yielded the highest average dentin adhesion Dark (non-photopolymerized) set time was evaluated using a modified version of ISO standard 7489. The measurement was performed under a yellow safelight at 21°-23° C., and resistance to indentation by a 400 g Gilmore needle was evaluated 60 seconds after the start of mixing and every 10 seconds thereafter. The cement of the invention had a set time of 11.5 minutes, and the control cement had a set time greater than 36 minutes.

EXAMPLE 3

Preparation of Powers Containing Oxidizing and Reducing Agents

A sample of the untreated Control Glass was slurry-treated with 0.1% potassium persulfate using the method of EXAMPLE 1. The treated glass was labeled "Glass B". A further sample of the Control Glass was slurry-treated with 0.5% ascorbic acid. The treated glass was labeled "Glass C". Equal portions of Glass B and Glass C were hand-mixed to provide a dry glass containing both an oxidizing agent and a reducing agent. This glass was labeled "Glass D".

When Glass D and the Control Liquid were combined in a 1.4:1 powder:liquid ratio and evaluated using the method of EXAMPLE 1, a cement with a CS of 152 MPa and a DTS of 28 MPa was obtained. The cement had an average measured adhesive shear bond strength of 7.8 MPa.

EXAMPLE 4

Cements Prepared from Liquids Containing Oxidizing Agent and Powders Containing Reducing Agent Several liquid solutions were prepared from the ingredients set out below in Table IVa:

TABLE IVa

| Ingredient | Parts |
|---|---|
| Copolymer of EXAMPLE 1 | 50 |
| Water | 30 |
| HEMA | 20 |
| $(C_6H_5)_2I^+PF_6^-$ | 0.7 |
| CPQ | 0.25 |
| BHT | 0.10 |
| $K_2S_2O_8$ | See Table IVb |

Several portions of a glass like the Control Glass of EXAMPLE 1 (but with a surface area of 3.3 $m^2/g$) were slurry-treated with various methanolic ascorbic acid solutions. The theoretical amounts of ascorbic acid on the treated glass are set out below in Table IVb.

Cements were formed by combining the treated glasses and liquids at a 1.4:1 powder:liquid ratio. Dark set times were tested according to ISO standard DIS 9917, using a 400 g indenter. Approximately 30 seconds were required to mix the cement, transfer it to the mold specified in the ISO standard, and place the mold in a 37° C. oven (also specified in the ISO standard). By then, some of the faster cements had already begun to set. These set times are indicated as "≦30" in Table IVb.

TABLE IVb

| | ISO SET Time, sec (dark) | | | | | | |
|---|---|---|---|---|---|---|---|
| % $K_2S_2O_8$ | % Ascorbic Acid on Glass | | | | | | |
| in Liquid | 0.05 | 0.10 | 0.25 | 0.5 | 1.0 | 1.5 | 2.0 |
| 0.025 | 600 | 400 | 360 | 280 | 240 | 120 | 100 |
| 0.05 | 330 | 280 | 230 | 120 | 80 | 70 | 80 |
| 0.10 | — | 160 | 70 | 50 | 50 | 40 | 40 |
| 0.25 | — | 100 | 50 | 40 | 40 | ≦30 | ≦30 |
| 0.5 | — | — | — | 40 | 35 | 35 | 35 |
| 1.0 | — | — | — | 35 | ≦30 | 35 | 35 |
| 1.5 | — | — | — | ≦30 | ≦30 | ≦30 | ≦30 |
| 2.0 | — | — | — | 35 | ≦30 | ≦30 | ≦30 |

The above data shows dark set times for cements containing varying amounts of reducing agent and oxidizing agent. The range of observed set times varied more than twenty-fold. Since the ISO test is performed at an elevated temperature (37° C.), room temperature set times likely would be longer.

EXAMPLE 5

Cements Prepared from Liquids Containing Oxidizing Agent and Inhibitor

The following liquid solutions were prepared:

TABLE V

| | Parts | | | |
|---|---|---|---|---|
| Ingredient | Control Liquid 2 | Liquid B | Liquid C | Liquid D |
| Copolymer of EXAMPLE 1 | 100 | 100 | 100 | 100 |
| Water | 60 | 60 | 60 | 60 |
| HEMA | 40 | 40 | 40 | 40 |
| CPQ | 1.0 | 1.0 | 1.0 | 1.0 |
| BHT | 0.1 | 0.1 | 0.1 | 0.1 |
| $K_2S_2O_8$ | 0.05 | 0.05 | 0.05 | 0.05 |

TABLE V-continued

| | Parts | | | |
|---|---|---|---|---|
| Ingredient | Control Liquid 2 | Liquid B | Liquid C | Liquid D |
| 4-methoxyphenol | — | 0.1 | 0.5 | 1.0 |

The untreated glass used in EXAMPLE 4 was slurry-treated by mixing together the ingredients set out below in Table VI. Each slurry was poured into a plastic-lined tray, dried overnight at 45° C., and then sieved through a 74 μm mesh screen to make Glasses E, F and G.

TABLE VI

| | Parts | | |
|---|---|---|---|
| Ingredient | Glass E | Glass F | Glass G |
| methanol | 40 | 40 | 40 |
| glass powder | 20 | 20 | 20 |
| diphenyliodonium chloride | 0.40 | 0.40 | 0.40 |
| ascorbic acid | 0.01 | 0.02 | 0.05 |

Dark set times were determined using the method of EXAMPLE 4. The results are set out below in Table VII.

TABLE VII

| | Dark set time, seconds | | |
|---|---|---|---|
| | Glass E | Glass F | Glass G |
| Control Liquid 2 | 330 | 280 | 230 |
| Liquid B | 870 | 840 | 510 |
| Liquid C | 930 | 840 | 810 |
| Liquid D | 900 | 870 | 810 |

The above data shows that adding 4-methoxphenol can increase set times, thus providing some measure of control over polymerization.

EXAMPLE 6

Cement Prepared Using Thiourea as Reducing Agent

20 Parts of the untreated glass of EXAMPLE 4 were slurried for 30 minutes in a solution of 0.15 parts thiourea in 40 parts methanol. The treated glass was dried overnight at 45° C. and sieved through a 74 μm mesh screen. A liquid solution was prepared from the ingredients set out below in Table VIII:

TABLE VIII

| Ingredient | Parts |
|---|---|
| Copolymer of EXAMPLE 1 | 50 |
| Water | 30 |
| HEMA | 20 |
| $(C_6H_5)_2I^+PF_6^-$ | 1.0 |
| CPQ | 0.25 |
| BHT | 0.10 |
| $K_2S_2O_8$ | 0.05 |

Cement mixes were prepared at a 1.4:1 powder:liquid ratio, placed in the ISO 9917 mold described in EXAMPLE 4, and photocured from above for 60 seconds using a VISILUX 2 dental curing light. "Barcol" hardness values were determined using a Barber-Colman hardness tester and indenter "GYZJ935". The measured hardness values were 51 on the top and 48 on the bottom of the molded cement sample, indicating that very uniform cure was obtained.

EXAMPLE 7

Cement Prepared from a Liquid Containing Polycarboxylic Acid Without Pendent Ethylenic Unsaturation A liquid solution containing a separate ethylenically-unsaturated ingredient was prepared by mixing together the ingredients set out below in Table IX:

TABLE IX

| Ingredient | Parts |
| --- | --- |
| 33% solution of polyacrylic acid ($M_w$ = 25,000) in water | 6 |
| HEMA | 4 |
| UDMA[1] | 0.3 |
| GDMA[2] | 0.3 |

[1] Trimethylhexamethylene diisocyanate end-capped at a 2:1 molar ratio with HEMA
[2] Glyceryl dimethacrylate A mixture of 0.8 parts Glass B and 0.8 parts Glass C was hand-spatulated with 1 part of the liquid. Using the method of EXAMPLE 2, a dark set time of 10 minutes, 10 seconds was observed. The average of the top and bottom Barcol hardness values after 1 hour was 43.

A control cement was prepared by mixing 1.6 parts of the untreated Control Glass with 1 part of the liquid. A dark set time of 50 minutes was observed. The average of the top and bottom Barcol hardness values after 1 hour was only 9.

EXAMPLE 8

Mixture of Commercial Cement Liquid with Powder Containing Oxidizing Agent and Reducing Agent 1 Part "GC Fuji LC" Liquid (the liquid portion of a commercial light-curable glass ionomer cement from GC Corp.) was hand-spatulated with 1.4 parts Glass D (which was made by combining 0.7 parts of the potassium persulfate-treated Glass B and 0.7 parts of the ascorbic acid-treated Glass C). Using the method of EXAMPLE 7, a dark set time of 10 minutes and an average Barcol harness after 2 hours of 72 were observed.

A control cement was prepared by hand-spatulating 1 part GC Fuji LC Liquid with the untreated Control Glass and stored under a yellow safelight. After 1 hour and 45 minutes, the mixture had not set.

This example demonstrates that a commercial light-curable glass ionomer cement can readily be modified to improve its dark set time.

EXAMPLE 9

Microencapsulation of $K_2S_2O_8$ in Cellulose Acetate Butyrate (CAB)

8.0 Parts CAB containing 18% butyl groups were dissolved in 800 parts methylene chloride. Separately, 5.0 parts $K_2S_2O_8$ were dissolved in 100 parts water. 330 Parts of the methylene chloride solution were transferred to a stainless steel vessel suspended in a room temperature water bath. A stirring impeller was suspended in the vessel and spun at 700 rpm. To the stirred solution was added 50 parts of the $K_2S_2O_8$ solution. The temperature of the water bath was raised to 37°–38° C., thereby slowly evaporating the methylene chloride. After one-half hour, ice was added to the water bath to lower the temperature to 24° C. 165 Parts n-hexane were added slowly to the vessel in order to precipitate the encapsulated oxidizing agent. The precipitate was filtered, washed with cold n-hexane and dried under vacuum. The resulting dry microcapsules were deagglomerated in an electric coffee grinder, yielding a very light fluffy powder.

EXAMPLE 10

Powder Containing Microencapsulated Oxidizing Agent and Unencapsulated Reducing Agent 67 Parts of the untreated glass used in EXAMPLE 4 were mixed on a roll mill for 1 hour with 0.232 parts of the microcapsules of EXAMPLE 9. 20 Parts of the resulting treated glass were mixed on a roll mill for one-half hour with 20 parts of a fresh sample of Glass C. The resulting mixture was labelled "Glass H". It was combined at a 1.4:1 powder:liquid ratio with Control Liquid 3 (a liquid like the Control Liquid of EXAMPLE 1, but containing 1 part rather than 0.7 parts $(C_6H_5)_2I^+PF_6^-$) and evaluated using the method of EXAMPLE 2. A set time of 12.5 minutes was observed.

Portions of Glass H were subjected to accelerated aging for 4 days and 8 days at 45° C. Set time measurements showed that the dark curing reaction was not slowed, thus indicating that the microcapsules had excellent storage stability.

EXAMPLE 11

Microencapsulation of Ascorbic Acid in CAB

3 Parts ascorbic acid were dissolved in 60 parts water. 8 Parts CAB were dissolved in 800 parts dichloromethane. 330 Parts of the CAB solution and 50 parts of the ascorbic acid solution were added to a stainless steel vessel and stirred at 708 rpm. A 38°–40° C. water bath was placed under the vessel. 165 Parts n-hexane were added slowly to the stirred mixture over a one-half hour period. A granular precipitate formed. Stirring was continued for 15 additional minutes. The warm water bath was replaced with an ice-water bath, resulting in the formation of additional precipitate. The precipitate was filtered, washed with n-hexane and dried under vacuum. The dried product was ground to a fine powder.

EXAMPLE 12

Silanol-treated Glass Powder Containing Microencapsulated $K_2S_2O_8$ and Ascorbic Acid 4 Parts "A-174" gamma-methacryloxypropyl trimethoxysilane (Union Carbide Corp.), 25 parts methanol, and 25 parts water were mixed, then acidified with trifluoroacetic acid until the pH reached 3.3. The mixture was stirred for 15 minutes at room temperature, yielding a silanol-containing treating solution. 100 Parts of a glass like the Control Glass of EXAMPLE 1 (but having a surface area of 2.8 $m^2/g$ rather than 2.6 $m^2/g$) were combined with the silanol treating solution, slurried for 1.5 hours at room temperature, dried overnight at 45° C., and sieved through a 74 μm mesh screen. A portion of the treated powder (5 parts) was mixed with 0.012 parts of the microencapsulated potassium persulfate of EXAMPLE 9. Another portion of the treated powder (5 parts) was mixed with 0.06 parts of the microencapsulated ascorbic acid of EXAMPLE 11. The two powder portions were combined and then roll-milled for one-half hour. The resulting blended powder was combined at a 2.2:1 powder:liquid ratio with Control Liquid 4 (a liquid like Control Liquid 3, but containing 0.05 parts BHT rather than 0.1 parts). The resulting cured cement was evaluated for CS and DTS using the method of EXAMPLE 1 (but with a 60 second photocure rather than 80 seconds). The respective CS and DTS values were 195 MPa and 38 MPa. If photocuring was omitted, the respective CS and DTS values were 180 MPa and 25 MPa.

Adhesion to enamel was evaluated by generally following the procedure of EXAMPLE 2. However, the potted teeth were ground to expose only the enamel surface. The polished enamel surface was etched for 15 seconds using gelled 37% phosphoric acid, washed for 30 seconds with water and then dried using compressed air. The measured adhesion to etched enamel was 18 MPa.

EXAMPLE 13

Microencapsulation by Precipitative Method

The three separate solutions whose compositions are set out below in Table X were each placed in separate addition funnels:

TABLE X

| Run No. | Solution |
|---|---|
| 1 | 3 parts ascorbic acid in 60 parts water |
| 2 | 3 parts $K_2S_2O_8$ in 60 parts water |
| 3 | 3 parts $(NH_4)_2S_2O_8$ in 60 parts water |

In a series of three separate runs, 50 parts of one of the solutions shown above were added to 366 parts of a stirred 1% solution of CAB in ethyl acetate contained in a stainless steel vessel immersed in a 4° C. water bath. The stirrer speed was maintained at 700 rpm and the bath temperature was maintained at 4° C. 267 Parts of ice cold n-hexane were added dropwise to the stirred solution over a 30 minute period. Granular spherical microcapsules were formed, as evidenced by microscopic examination. Stirring was continued for an additional 15 minutes. The granular precipitate was filtered, washed with ice-cold n-hexane, dried under vacuum and then deagglomerated in an electric coffee mill.

EXAMPLE 14

Preparation of Tri-Cure Cement from Silanol-Treated Glass Powder

To 100 parts of a silanol-treated glass like that of EXAMPLE 12 were added 0.55 parts of the ascorbic acid microcapsules of Run no. 1 of EXAMPLE 13, and 0.1 parts of the $K_2S_2O_8$ microcapsules of Run no. 2 of EXAMPLE 13. The mixture was mixed on a roll mill for 1 hour. Using the method of EXAMPLE 4, the dark set time was determined to be 4 minutes, 20 seconds. Using the method of EXAMPLE 12, the respective CS and DTS values after light-curing were determined to be 210 MPa and 31 MPa.

EXAMPLE 15

Preparation of Tri-Cure Cement from Microencapsulated $(NH_4)_2S_2O_8$ and Ascorbic Acid A solution of 2 parts A174 silane, 12.5 parts methanol, 12.5 parts water and 0.22 parts acetic acid was stirred for 30 minutes, combined with 50 parts of the untreated glass of EXAMPLE 12, slurried for 1.5 hours at room temperature, dried overnight at 45° C., and sieved through a 74 μm mesh screen.

20 Parts of the resultant powder were added to 0.11 parts of the microencapsulated ascorbic acid of Run no. 1 of EXAMPLE 13 and 0.02 parts of the microencapsulated ammonium persulfate of Run no. 3 of EXAMPLE 13. The powders were mixed by roll-milling for about 1 hour. When evaluated as in EXAMPLE 14, the dark set time was determined to be 4 minutes, 20 seconds, and the CS and DTS values were determined to be 208 MPa and 30 MPa.

EXAMPLE 15

Modification of Commercial Cements

In a first run, 4.5 parts "GC Fuji LC" light-curable glass ionomer cement were combined with 0.025 parts of the ascorbic acid microcapsules of Run no. 1 of EXAMPLE 13 and 0.0045 parts of the potassium persulfate microcapsules of Run no. 2 of EXAMPLE 13. The resulting powder mixture was roll-milled for one half hour. The powder was labeled "Modified GC Glass".

As a second run, 4.1 parts "Kerr XR" ionomer powder (Kerr Division of Sybron, Inc.) were combined with 0.0336 parts of the ascorbic acid microcapsules and 0.0044 parts of the potassium persulfate microcapsules. After roll-milling, the resulting powder was labelled "Modified Kerr Glass".

The modified glasses and the unmodified commercial glasses were independently combined at a 1.4:1 powder:liquid ratio with the corresponding commercial liquids supplied by the manufacturers, and permitted to harden without photocuring. The resulting cements were evaluated for room temperature and ISO dark set time using the methods of EXAMPLES 2 and 4. The cements were also evaluated for Barcol hardness using the method of EXAMPLE 6. Set out below in Tables XIa and XIb are the set time and Barcol hardness values for each cement.

TABLE XIa

|  | GC Cement | | Kerr Cement | |
|---|---|---|---|---|
|  | Unmodified | Modified | Unmodified | Modified |
| | Dark Set Time | | | |
| Room Temperature | 35 min | 12 min 30 sec | 35 min | 12 min 30 sec |
| ISO (37° C.) | 8 min 40 sec | 5 min 20 sec | 14 min | 5 min 40 sec |
| | Barcol Hardness | | | |
| Room Temperature | | | | |
| After 15 minutes | 0 | 23 | 0 | 0 |
| After one hour | 15 | 47 | 0 | 24 |
| ISO (37° C.) | | | | |
| After 15 minutes | 22 | 22 | 0 | 0 |
| After one hour | 34 | 54 | 8 | 34 |

As the above data illustrates, under dark conditions the modified cements set more rapidly and reached a higher ultimate hardness than the unmodified cements. The modified cements would therefore be much better suited to deep cure restorations, cure without a light or with a faulty light, and other low light situations.

Although this invention has been described using certain illustrative examples, it should be understood that the invention is not limited to the specific exemplary embodiments shown in this specification.

We claim:

1. A water-containing, ionically-hardenable, photocurable, ethylenically-unsaturated dental cement, comprising
   a) finely-divided acid-reactive filler,
   b) water-miscible acidic polymer,
   c) photoinitiator,
   d) water-soluble reducing agent, and
   e) water-soluble oxidizing agent,
wherein the reducing agent and the oxidizing agent are capable of initiating gelation of a 10:10:1 weight basis water:acrylamide:methylene bis-acrylamide mixture.

2. A cement according to claim 1, wherein the filler comprises metal oxide, metal salt or glass.

3. A cement according to claim 2, wherein the glass comprises fluoroaluminosilicate glass.

4. A cement according to claim 1, wherein the polymer comprises a homopolymer or copolymer of an alkenoic acid.

5. A cement according to claim 4, wherein the polymer comprises a copolymer of acrylic acid containing one or more ethylenically-unsaturated groups.

6. A cement according to claim 1, containing as a further component an ethylenically-unsaturated monomer.

7. A cement according to claim 1, wherein the reducing agent is selected from the group consisting of ascorbic acid, cobalt (II) chloride, ferrous chloride, ferrous sulfate, hydrazine, oxalic acid, thiourea, and salts of a dithionite or sulfite anion.

8. A cement according to claim 1, wherein the reducing agent comprises ascorbic acid or thiourea.

9. A cement according to claim 1, wherein the oxidizing agent is selected from the group consisting of cobalt (III) chloride, tert-butyl hydroperoxide, ferric chloride, perboric acid and its salts, and salts of a permanganate or persulfate anion.

10. A cement according to claim 1, wherein the oxidizing agent comprises potassium or ammonium persulfate.

11. A cement according to claim 1, wherein the cement has two parts respectively containing glass and polymer, and one agent is packaged with the glass and the other agent is packaged with the polymer.

12. A cement according to claim 1, wherein at least one of the agents is microencapsulated.

13. A cement according to claim 12, wherein the cement has two parts respectively containing glass and polymer, and both agents are packaged with the glass.

14. A cement according to claim 12, wherein the cement has two parts respectively containing glass and polymer, and both agents are packaged with the polymer.

15. A cement according to claim 12, wherein at least one of the agents is microencapsulated with water-soluble encapsulant.

16. A cement according to claim 12, wherein at least one of the agents is microencapsulated with water-insoluble encapsulant.

17. A cement according to claim 16, wherein the encapsulant comprises cellulose acetate butyrate.

18. A cement according to claim 1, wherein the cement contains about 3% to about 25% water, about 25% to about 85% filler, about 10% to about 50% polymer, about 0.1% to about 5% photoinitiator, about 0.02% to about 5% reducing agent, and about 0.02% to about 5% oxidizing agent.

19. A cement according to claim 18, wherein the cement contains about 5% to about 20% water, about 50% to about 75% filler and about 10% to about 30% polymer.

20. A dental cement powder, comprising finely-divided acid-reactive filler, a water-soluble reducing agent and a water-soluble oxidizing agent, at least one of the agents being microencapsulated, wherein the reducing agent and the oxidizing agent are capable of initiating gelation of a 10:10:1 weight basis water:acrylamide:methylene bisacrylamide mixture.

21. A dental cement liquid, comprising water-miscible acidic polymer, a water-soluble reducing agent and a water-soluble oxidizing agent, at least one of the agents being microencapsulated, wherein the reducing agent and the oxidizing agent are capable of initiating gelation of a 10:10:1 weight basis water:acrylamide:methylene bis-acrylamide mixture.

22. A liquid according to claim 21, further comprising an ethylenically-unsaturated moiety.

UNITED STATES PATENT AND TRADEMARK OFFICE
CERTIFICATE OF CORRECTION

PATENT NO. : 5,154,762

DATED : October 13, 1992

INVENTOR(S) : Mitra et al.

It is certified that error appears in the above-identified patent and that said Letters Patent is hereby corrected as shown below:

Col. 4, lines 39/40, "No. 0 323  20" should be
    --No. 0 323 120--.

Col. 5, lines 55/56, "acrylam bis-acrylamide" should be
    --acrylamide:methylene bis-acrylamide--.

Col. 6, line 28 "tions Although" should be
    --tions.  Although--.

Col. 6, line 37, "($T_9$)" should be --($T_g$)--.

Col. 9, line 59, "posed Further" should be
    --posed.  Further--.

UNITED STATES PATENT AND TRADEMARK OFFICE
CERTIFICATE OF CORRECTION

PATENT NO.  : 5,154,762
DATED       : October 13, 1992
INVENTOR(S) : Mitra et al It is certified that error appears in the above-indentified patent and that said Letters Patent is hereby corrected as shown below:

```
Col. 10, line 51, "Powers" should be --Powders--.

Col. 18, line 36, "bisacrylamide" should be
   --bis-acrylamide--.
```

Signed and Sealed this

Twenty-sixth Day of October, 1993

Attest:

BRUCE LEHMAN

Attesting Officer

Commissioner of Patents and Trademarks